United States Patent [19]

Prestwich

[11] Patent Number: 4,582,901
[45] Date of Patent: Apr. 15, 1986

[54] FLUORINATED CELLULOSE ESTERS AND THE USE THEREOF AS TERMITICIDAL COMPOSITIONS

[75] Inventor: Glenn D. Prestwich, St. James, N.Y.

[73] Assignee: The Research Foundation of State University of New York, Albany, N.Y.

[21] Appl. No.: 639,122

[22] Filed: Aug. 9, 1984

[51] Int. Cl.$^4$ .................... C08B 3/00; A61K 31/72; A61K 31/735

[52] U.S. Cl. .................... 536/83; 424/DIG. 11; 536/58; 536/63

[58] Field of Search ............ 424/DIG. 11, 180, 362; 536/58, 63, 83

[56] References Cited

U.S. PATENT DOCUMENTS

| | | | |
|---|---|---|---|
| 1,687,060 | 10/1928 | Clarke et al. | 536/83 |
| 2,980,491 | 4/1961 | Segal et al. | 536/63 |
| 2,992,881 | 7/1961 | Berni et al. | 536/63 |
| 4,092,110 | 5/1978 | Adolphi et al. | 424/DIG. 11 |
| 4,455,441 | 6/1984 | Prestwich | 424/DIG. 11 |

FOREIGN PATENT DOCUMENTS 48-56294 8/1973 Japan .................... 536/83

OTHER PUBLICATIONS

Prestwich et al., "Flourolipids as Targeted Termiticides and Biochemical Probes", Journal of Agric. and Food Chem., (1981), 29: 1023–1027, American Chemical Society, Easton, PA.

*Primary Examiner*—Ronald W. Griffin
*Attorney, Agent, or Firm*—Omri M. Behr

[57] ABSTRACT

Cellulose is modified by the provision of up to 5% by weight of fluorinated ester groups. This material is substantially indistinguishable from cellulose by termites seeking food but is sufficiently toxic to them to be utilizeable as a highly efficient termiticide while being relatively harmless to mammals.

21 Claims, 1 Drawing Figure

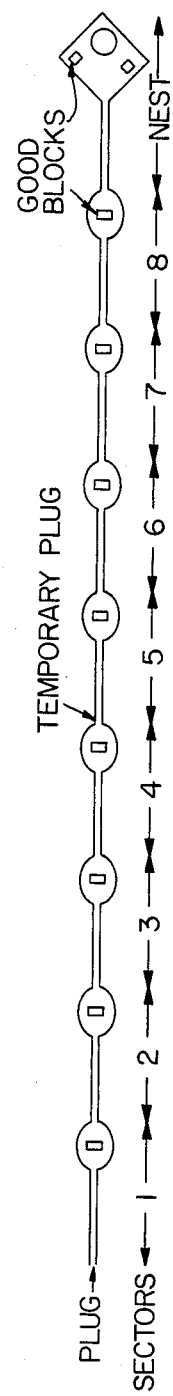

FLUORINATED CELLULOSE ESTERS AND THE USE THEREOF AS TERMITICIDAL COMPOSITIONS

BACKGROUND OF THE INVENTION

Termites, and related pests, constitute a significant economic threat in a modern society. While conventional insecticides, typically chlorinated hydrocarbons such as chlordane, DDT, aldrin, dieldrin and BHC can be effectively utilized to eradicate these pests, such insecticides pollute water, contaminate soil, and are toxic to many life forms. Chlordane is the only chlorinated hydrocarbon that has not yet been banned, principally because a suitable substitute having its effectiveness has yet to be found. However, it still accumulates in the environment and causes food chain elimination since, for instance, an earthworm may be resistant to its poison, but the bird which consumes many such earthworms may die or be rendered infertile. A environmentally inactive chemical is thus needed to obviate food chain problems. While the chlorinated hydrocarbon insecticides are economical to produce, the cost of the resulting environmental cleanup makes their use expensive in the long run. Thus, there exists a substantial need for new environmentally safe and effective pesticides.

For a pesticide to be effective against termites and related pests it may have a somewhat delayed onset of activity. Termites typically feast upon a food supply and then return to their nest and regurgitate the food to be shared by those occupying the nest. Thus, a pesticide which instantly destroys the feeding termites has absolutely no effect upon those hatching on the nest. While the feeding termites are affected, those in the nest continue to multiply and thus the infestation remains.

Termiticidal compositions which meet the foregoing criteria have been prepared by Applicant and are disclosed in Prestwich, U.S. Pat. No. 4,452,793 and Prestwich, U.S. Pat. No. 4,455,441.

While these termiticidal compostions represent a substantial improvement over the prior art, they still require to be adsorbed upon suitable carriers.

These compounds show excellent differential toxicity. That is to say, that the level of toxicity, i.e., $LD_{50}$ (for termites), is substantially greater than that for mammals. In the interests of further environmental safety, it would be desirable to provide attractant termiticidal compositions which are chemically bound to the carrier rather than merely adsorbed thereon, in order to further reduce the possibility of environmental contamination by leaching, small though this possibility may be.

Since cellulose is the favorite source of nourishment for termites, it would be desirable to chemically modify cellulose in a manner which would meet these criteria. In designing such a termiticide however care must be taken to ensure that the modified material would be substantially indistinguishable, in a physical sense, from cellulose itself so that the termites would feed upon it without realizing its toxic nature. Furthermore, the modification of the cellulose could be such as to maintain the delayed toxicity factors which have made the previously disclosed Prestwich compositions commercially desirable.

SUMMARY OF THE INVENTION

The termiticidal compositions of the present invention comprise cellulose which has been modified to include fluorinated ester moieties. These fluorinated ester moieties fall in two categories. Those wherein the fluoro atom or atoms are on the acyl residue of the ester and those wherein the fluorine is on the alkoxy moiety of the ester. Since the mechanism of poisoning operates by enzymic cleavage of the ester group by the enzymes present in the digestive tract of the termite followed by absorption by the termite of the fluorinated residue, these two categories of compounds should be regarded as essentially equivalent. Two general methods are available for the preparation of the compositions of the first category and one method for the second.

In the first category, the starting material is cellulose itself which is reacted with a fluoroacylic acid in the presence of a carbodiimide. While this method is operative from a chemical standpoint to yield the desired products, these contain insoluble adducts of carbodiimide and the fluoroacylic acid itself which tend to have a higher level of toxicity then the desired adduct itself. While these undesired adducts can be removed by extensive washing, this unnecessarily adds to the cost of the product.

The compounds of the first category may also be prepared by reacting cellulose directly with a fluoroacylchloride in the presence of non-aqueous base.

The compositions of the second category are made utilizing as starting material partially carbomethoxylated cellulose which is a readily available chromatographic substrate. This material is then reacted with a suitable fluoroalkanol by the carbodiimide method set forth hereinabove.

The fluorinated products of the present invention are suitably used in one of three forms. The compositions may be made up into a paste and molded to form bait blocks which are then placed around the structures to be protected, or around the suspected nests of the termites. The material may per contra be put up in finely divided form and injected as a dust into the interstitial areas of structures to be protected. Such finely divided dust can be readily blown into crevices into the which the termites might proceed.

Finally, the cellulose used for the formation of the compositions may be wooden blocks which are then surface treated by the methods discussed hereinabove to provide the fluorinated compositions.

DESCRIPTION OF THE PREFERRED EMBODIMENT

The partially fluoroacylated cellulose compositions of the present invention have a predetermined number of acylatable sites which are acylated by fluoroacyl groups, the weight of said fluoroacyl groups comprise between about 0.05 and 5% by weight of the total composition. The acyl moieties are alkanoyl, alkenoyl, or polyalkenoyl moieties of 1 to 20 carbon atoms. It is especially preferred to prepare compositions where the fluoroacyl moiety comprises between 0.05 and 0.5, by weight of the entire composition. While higher percentages of fluoroacyl moieties would be effective from a termiticidal point of view, such compositions have a physical texture different from that of the unmodified cellulose itself, while compositions in the preferred range, i.e., less than 5% fluoroacetylation are substantially physically indistinguishable from the cellulose itself, and thus contribute to "fooling" the termites.

Among the acyl moieties which may be utilized are acetyl, butyryl, hexanoyl and higher even-carbon number alkanoyl alkenoyl, or alkpolyenoyl.

These may be substituted by one or more fluorine atoms. It has been found however, that toxicity is decreased by the substitution of more than one fluorine per carbon atom. It has further been found that the toxicity level is inverse proportion to the chain length. Thus, the fluoroacetyl moiety is especially preferred since it results in the highest level of termiticidal toxicity. Thus, while all fluorinated acyl moieties cited herein are to be considered to be within the scope of the present invention, the fluoroacetyl moiety or as ω-fluoro acyl moieties is especially preferred.

It has further been found that the efficacy of the compositions is related to the purity of the cellulose itself. Thus, while bulk powdered alpha-cellulose is operative as a substrate, the best results were obtained utilizing a Whatman Cellulose Fibre Powder or equivalent acylation grade cellulose material.

In the preferred mode of preparation, the cellulose powder is dried, suitably by azeotropic drying with an azeotroping solvent such as benzene, toluene, and the like, toluene being especially preferred. After drying, the cellulose powder is suspended in approximately 8 times its weight of the solvent, suitably toluene, a suitable organic base preferably a pyridine, is added in substantial excess of the acyl halide to be added. The mixture cooled and the predetermined amount of acyl halide in the bulk solvent is added dropwise. The reaction should be considered to be substantially quantitative. Thus, for a loading of about 0.25% of fluoroacetate, there would be employed about 3 ml. of fluoroacetyl chloride per 500 grams of cellulose powder.

The reaction mixture, after completion of the addition, is stirred for from about 12 to 30 hours at ambient temperatures, filtered, and washed successively with polar organic solvents, polar organic solvent/water, water, dilute mineral acid, and water to yield a substantially neutral filtrate. The residual solid is then dried. In the alternative mode the cellulose is dried in a similar manner, slurried in the solvent and treated with a predetermined amount of fluoracetic acid in the presence of an organic base such as dimethylaminopyridine (about 0.05 to about 0.5 molar equivalents) and ethyl-N,N'-dimethylaminopropyl carbodiimide (about 1 to about 2 molar equivalents). Other bases such as collidine, butidine, triethylamine or other non-aqueous organic base or other carbodiimides such as N,N-dicyclohexylcarbodiimide and related compounds may also be employed. The slurries are shaken for from about 24 to about 48 hours at between about 20° and about 40° C. and then washed in the manner set forth above for the first mode of preparation. The thus obtained product contains not only the desired fluoroacetylated cellulose but also covalent or insoluble carbodiimide and fluoroacetic acid. These adducts cannot be removed by repeated washing.

The second group of compositions within the scope of the present invention are the fluoroalkyl esters of partially carbomethoxylated cellulose which is an article of commerce. Carbomethoxycellulose having a carbomethoxy loading of approximately 1 to 50% by weight is generally available as a chromatographic substrate and is sold under the name of CM Cellulose. This material may be esterified with any fluorinated alcohol containing 1 to 20 carbon atoms and sustituted by between 1 to 20 fluorine atoms. It is preferred that there be not more than one fluorine atom per carbon atom. Since the moiety of greatest toxicity contains the grouping F—C—C, it is especially preferred to utilize 2-fluoroethanol or ethylene fluorohydrin as the preferred alkanol.

The procedure utilized is the standard carbodiimide procedure. In this procedure the substrate, that is to say, the CM cellulose, is first converted to the acid form, dried by refluxing in an azeotropic solvent such as toluene, xylene, benzene or the like, until no further water is abstracted. The thus produced slurry is then treated with a predetermined amount of the fluoroalkanol in the presence of an organic base, suitably dimethylaminopyridine and the appropriate carbodiimide, for example, ethyl-N,N'-dimethylaminopropylcarbodiimide. The materials are shaken for between 20 and 40 hours at between 20° and 40° C. and then washed in the manner set forth above to yield the desired materials.

The reaction should be considered to be substantially quantitative.

The compositions of the present invention are preferably used in two different modes. The first serving as a termiticide for structures already believed to be infested with termites and the other as a protective mechanism external of such structures and in locations proximate to the location of termite nests.

In the first mode the active composition is formulated as a dust. This mode is particularly effective for dry wood termites. This dust is formulated from the compositions by physical methods well known in the art and has a particle size of between 5 and 75 microns. The dust is then blown into the interstitital spaces of structures known or believed to be infested by termites and because of its finely divided nature will insinuate itself into those areas through which the termites will travel. Since termites are known to prefer finely divided cellulose over solid cellulose, they will show a preference for the dust and, in their normal manner of operation, carry it back to the nest where it will be regurgitated and serve to poison other members of the nest.

The more usual mode of protection against termites, especially subterranean, is to bury the termiticidal composition, suitably in the form of bait blocks, around the structures to be protected and, if known, around the location of the termite nests. Such bait blocks being readily acceptable to the termites are usually attacked in preference to the structures and the poisoned material carried back to the nest.

In the general mode of formulation, the fluorinated cellulose compositions are mixed with a suitable cellulosic diluent in a diluent: fluorinated cellulose ratio of between 40 to 1 and 1 to 1. While any readily available cellulosic diluent may be utilized, fluting paper pulp is especially preferred because its characteristics are highly desirable to termites.

The components are dry-mixed, suspended in water and then drained through a screen to provide mats. In order to make the material attractive to the termites, it is preferred that the pulp material, prior to making of the mat is pulverized to a short fiber length, preferably less than 0.25 millimeters. This fiber length however, reduces the mechanical strength of the mat. For this reason, the mats are generally inserted into plastic sleeves which are then buried in the desired locations. These plastic sleeves, which are open at the ends serve to protect the mats mechanically but permit the termites to have ready access.

BRIEF DESCRIPTION OF THE DRAWING

FIG. I represents an apparatus useful for field testing termiticidal compositions.

EXPERIMENTAL TESTING

Dust Injection

This assay is a simulation of a field test for dry wood termite control. *R. flavipes* is used in the simulation experiment using the apparatus shown in FIG. I.

Numbered sectors: glass tube (15×ID 0.5 cm)+plastic petri dish (5.0×1.2 cm)

Nest sector: tube+3×11×11 cm plastic sandwich box with artificial nest (plastic cylinder (5.0×2.5 cm) filled ¾ full with wet sand and a paper pulp disc+2 g termites)

Food blocks: in sectors 1 and 5 were flute pulp blocks in all other sectors were white blotter paper blocks.

Termites: The termites (*R. flavipes* collected at Janesville, WI. and maintained in lab at 25° C.; 462 termites, includes 1 soldier/2 g) were given one day to acclimate to the unit. Termites were chased out of sectors 1 to 4 and a plug was inserted at sector 4 as shown. Flaxcel II-CF powder (see Example IV) containing 0.286% w/w fluoroacetate was blown into the distal end and distributed through sectors 1 to 4.

Results

When the plug at sector 4 was removed, termites immediately re-entered the treated zone and exhibited no avoidance or walling-off behavior thereafter. Numerical results follow:

| Rep. | Number of dead termites at | | | 7 days (terminated) | % biomass of survivors | Distribution of final no. dea/no. alive in sector | | | | | | | | |
|------|------|------|------|------|------|------|------|------|------|------|------|------|------|------|
|      | 8 hr. | 1 day | 2 day | | | 1 | 2 | 3 | 4 | 5 | 6 | 7 | 8 | nest |
| A    | 0 | 34 | 314 | 366 | 15.05 | 145 | 64 | 26 | 20 | (10) 53 | (14) 30 | (2) 8 | (15) 15 | (51) 5 | (alive) dead |
| B    | 0 | 16 | 177 | 201 | 40.55 | 82 | 38 | 10 | 12 | (1) 18 | (23) 19 | (22) 11 | (16) 5 | (169) 6 | (alive) dead |
| C    | 0 | 13 | 213 | 263 | 28.10 | 105 | 62 | 35 | 17 | (1) (28) 14 | (82) (26) 10 | (6) 8 | (1) 5 | (27) 12 | (alive) dead |
| mean % | 0% | 4.5% | 50% | 60% | 28% | | | | | | | | | |

Conclusion

The dust-free injection treatment revealed no avoidance, delayed onset of toxicity, and good mortality at the 7 day termination.

Bioassay of Flaxcel II-CF with *Reticulitermes Flavipes* Baits

Baits used in the new were 4"×4" made by admixing the cellulose CF-11 (control of Flaxcel in various ratios with fluting paper pulp (the convoluted element in corrugated boxboard). This pulp is comparable to *G. trabeum*-decayed wood as a highly preferred food material (both in lab and field tests). The pulp was pulverized to 0.25 mm fiber length because *R. flavipes* seem to prefer the shorter fibers.

The mats were made as follows: 8 g. pulp+2 g. or 8 g of Flaxcel II-CF were dry mixed in a blender for 1 minute. The mix was put into 4"×4" frame with a very fine screen bottom and spread as a level layer. This was pressed down on a wet sponge to minimize the loss of fine particles and air dried. The fluoroacetylated cellulose is homogeneously distributed through the bait.

The mats are somewhat fragile because of the short fiber length of the pulp, especially the mats with 1:1 pulp and fluoroacetylcellulose. The mats can best be cut to bait block sizes with a jig-saw or scissors.

No-choice Flaxcel II-CF blocks

To a zipper case (2" diam.×2") was added 10 g. sand, 3 ml. H₂O and 0.50 g. termites (mixed casts, freshly collected *R. flavipes* from Stony Brook), a 1 cm³ square of Flaxcel-II-CF mat was added and the termites were allowed to feed ad libitum for 7 days. Control was a cube of *G. trabeum*-rotted sweet gum. Six replicates were performed for each treatment.

| Flaxcel Mat (ppm Fluoroacetate) | Mean Biomass Survivors (%)* | Mean Food Consumed (% eaten) |
|---|---|---|
| 0 | 0.15 ± .03 (32%) | .063 g/.21 g. (30%) |
| 1430 | 0 (no survival) | .01/.16 (4%) |
| 572 | 0.2 ± .01 g. (3%) | .02/.12 (17%) |

*Low count due to cannibalism and difficulty with termite recovery.

COMPARATIVE TOXICITY TESTS (a) Toxicity of Flaxcel II-CF in Comparison to Non-covalently Bound Fluoroacetate Non-covalently bound sodium fluoroacetate and various concentrations of fluoroacetate in Flaxcel II-CF were added to the diet of *Trichoplusia ni* larvae. The results are set forth in the following table.

| Flaxcel II-CF weight % of diet | Fluoroacetate, ppm in diet | (mean ± S.D. for 3 replicates of 10 larvae each) Mortality, Day 3 |
|---|---|---|
| 12.5% | 358 ppm | 100% |
| 5.0 | 143 | 80 ± 17 |
| 1.25 | 36 | 46.7 ± 12 |
| 0.5 | 14 | 30 ± 10 |
| 0.125 | 4 | 23 ± 15 |
| 21.5% CF-II Cellulose Control | 0 | 13.2 ± 15 |

An LC₅₀ was observed for non-covalently bound fluoroacetate of 0.5 ppm. Assuming similar sensitivity of the two larvae, then Flaxcel II-CF is 80× less toxic than fluoroacetate to caterpillars.

Mammalian Toxicity of Flaxcel II-CF (Rats)

The dose was prepared as a paste with a carrier solvent containing 33% Emulphor emulsifier (GAF Corp.) and 67% water. The ratio of Flaxcel II-CF to carrier solvent was 0.15:1 (w/v).

Two male rats received on oral dose at the rate of 1 g/kg and another 2 male rats at 4.5 g/kg (given in 3 subdoses of 1.5 g/kg every 2 hrs). No symptoms of toxicity occurred during the 14 day observation period. The same results were obtained with female rats.

In another experiment, one male rat died few minutes after receiving a third dose (total doses 5 g/kg at 1.67 g/kg every 1.5 hrs). The other male and two female rats received 5 subdoses (total doses 8.3 g/kg) and all died during the night following the administration.

A control experiment was also carried out. Two male and two female rats were each administered 5 subdoses of cellulose paste (preparation and dosing schedule same as above for a total of 8.3 g/kg). One female rat was dead during the night. The remaining three rats showed some symptoms of toxicity but recovered 2 days later.

The oral acute toxicity of Flaxcel II-CF (fluoroacetate loading 0.286% w/w) in rats was determined. Based on the test results, the estimated $LD_{50}$ of this compound in rats is 3-5 g/kg.

The above results indicate that fluoroacetate was only partially released from Flaxcel II-CF in the GI tract of rats. If all of the fluoroacetate was released from Flaxcel II-CF, a $LD_{50}$ of 0.4-1 g/kg would be expected. The $LD_{50}$ of sodium fluoroacetate was reported to be 2-5 mg/kg (The Merck Index, 1968).

EXAMPLE I

Synthesis of Fluoroacetylcellulose

Carbodiimide methods. Cellulose (ICN, bulk powdered alphacellulose) was dried by azeotropic removal of water. Thus, 40 g. of alphacel was refluxed under a drying tube with 250 ml benzene until no further water accummulated in the Dean-Stark trap (4 h). The slurry was divided into four equal portions to make different levels of fluoroacetate loading. Thus, into four 100-ml. round bottom flasks, was placed ca. 10 g. of dry alphacel as the benzene slurry, and the following quantities of fluoroacetic acid (Columbia Organics), 4-dimethylamino pyridine (Aldrich, DMAP, 0.2 molar equiv.), ethyl N,N-dimethylaminopropyl carbodiimide (Sigma, EDCI, 1.3 molar equiv.).

| Nominal Loading | Name of Preparation | Fluoroacetic Acid | DMAP | EDCI |
|---|---|---|---|---|
| 1% | Flaxcel 100 | 100 mg. | 24 mg. | 320 mg. |
| 0.3% | Flaxcel 30 | 30 mg. | 8 mg. | 108 mg. |
| 0.1% | Flaxcel 10 | 10 mg. | 4 mg. | 32 mg. |
| 0.03% | Flaxcel 3 | 3 mg. | 2 mg. | 11 mg. |

The slurries were capped and swirled on an orbital shaker for 36 hrs. at 30°. The fluoroacetyl cellulose samples were washed exhaustively (20 volumes each) with benzene, benzene-acetone, acetone, acetone-water, 1N HCl water, 0.1% NaHCO$_3$ and then with water to neutrality. Samples were dried at 80° C. until powdery. The Flaxcel 100 had 43.11% C, 6.44% H, 0.75% N, and 0.28% F, and therefore contained covalent or insoluble adducts of the carbodiimide and fluoroacetic acid.

In accordance with the above procedure but where in place of EDCI there is utilized N,N-dicyclohexyl carbodiimide in toluene/THF (4:1) solvent, the same product is obtained.

EXAMPLE II

Synthesis of Acetylcellulose

A sample of 1% acetylcellulose (Axcel 100) was prepared by an identical procedure to that of Example I, substituting 100 mg acetic acid for the fluoroacetic acid. This material showed negligible incorporation of EDCI-derived impurities, C 43.17%, H 6.13%, N 0.008%; untreated alphacel showed C 43.07%, H 6.20%, N 0.006%.

EXAMPLE III

Fluoroacetyl Chloride Method

Fluoroacetyl chloride (Warning: volatile poison; use well ventilated hood) as prepared. To 21.2 g (195 mmole) of sodium fluoroacetate (90% grade, Sigma) was added 32 ml (44.7 g, 220 mmole) phthaloyl dichloride (Aldrich) in a round bottom flask fitted with a distillation head. The flask was heated from 25° to 140° and after discarding a 1 ml forerun (after 1N NaOH hydrolysis!), about 20 ml of pure fluoroacetyl chloride, (bp 68°-71° C.) (lit.bp 70°-71°, n$_D$ 1.382) was collected. Then, to a stirred suspension of 20 g of dry alphacel in 80 ml toluene was added 3 ml of pyridine, 10 mg of DMAP, and (dropwise) a solution of 0.20 ml of fluoroacetyl chloride in 10 ml toluene. The mixture was stirred 80 hrs. at 20° and worked up by filtration and exhaustive washing with toluene, toluene-acetone, acetone, acetone-water, water, 0.2N HCl, water, 0.1N NaHCO$_3$, and water to neutrality. The "Flaxcel-II" was dried an showed C 43.36%, H 5.96%, and F 0.020%, indicating that approximately 0.064% fluoroacetate loading had been achieved by this method. (Fluoroacetate loading w/w %=% Fx 61/19).

EXAMPLE IV

A larger preparation of Flaxcel-II-CF was performed as follows. Whatman Cellulose Fibrous Powder CF-II (500 g) was dried by azeotropic removal of water with toluene (3 l) in a 5-l flask (8 ml H$_2$O removed). After cooling to room temperature, 250 mg of 4-dimethylaminopyridine, 100 ml of distilled pyridine and an additional 1 l. of toluene were added. The solution was cooled and stirred mechanically as a solution of 10 ml of fluoroacetyl chloride in 100 ml toluene was added dropwise during 0.5 hr. The mixture was stirred 20 hr. at ambient temperature, filtered, and washed (by resuspension) with 3 l. toluene-acetone (2:1), 3 l. of acetone; 3 l. of acetone-water (2:1), 2×3 l. of water; 3 l. of 0.1N HCl, and 6×3 l. of water to give a filtrate with pH 5.5 (same as H$_2$O used). This was sucked dry and dried at 80° C. for 6 hr. Analysis C 43.58%, H 6.24, F 0.089 (0.286% loading of fluoroacetate (w/w).

Similarly, but where in place of fluoro acetic acid, there is utilized 4-fluorobutyric acid, 6-fluorohexanoic acid, an even-carbon ω-fluoroacids thru 16-fluorohexadecanoic acid, there are obtained the corresponding fluoroacylated cellulose.

EXAMPLE V

Synthesis of Fluoroethoxycarbomethoxy cellulose

Carbomethoxy cellulose (CM Cellulose) was converted to the acid form by washing with 1N HCl and then was dried by azeotropic removal of water. Thus, 10 g. of acid CM Cellulose was refluxed under a drying tube with 75 ml benzene until no further water accummulated in the Dean-Stark trap (4 h). The slurry is charged to a 100-ml. round bottom flask, as the benzene slurry, ethylene fluorohydrin (10 mg., Columbia Organics), 4-dimethylamino pyridine (Aldrich, DMAP, 4 mg., 0.2 molar equiv), ethyl N,N-dimethylaminopropyl carbodiimide (Sigma, EDCI, 32 mg., 1.3 molar equiv.). The slurries are capped and swirled on an orbital shaker for 36 hrs. at 30°. The fluoroethoxylated cellulose samples were washed exhaustively (20 volumes each) with benzene, benzene-acetone, acetone, acetone-water, 1N HCl water, 0.1% NaHCO₃ and then with water to neutrality. Samples are dried at 80° C. until powdery.

In accordance with the above procedure but where in place of EDCI there is utilized dicyclohexyl carbodiimide (DCC) the same product is obtained.

Similarly, but where in place of ethylenefluorohydrin there is utilized 4-fluorobutanol, 6-fluorohexanol, 10-fluoro-Z-3-decanol, 12-fluoro-Z,Z-3,6-dodecandienol or other ω-fluoroalkanols and alkenols, there are obtained the corresponding fluorocellulose, alkyl and alkenyloxy carbomethoxy cellulose.

I claim:

1. Cellulose comprising ester moieties having a substituted fluorine atom thereon, said fluorinated ester moieties comprising between 0.05 and 5% by weight of the total composition.

2. A partially fluoroacylated cellulose composition of claim 1 wherein a predetermined number of acylatable sites are acylated by fluoroacyl groups, said fluoroacyl groups comprising between 0.05 and 5% by weight of the total composition wherein the acyl moieties are straight or branched chain alkanoyl, alkenoyl, or alkpolyenoyl moieties containing 2 to 20 carbon atoms and being substituted by between 1 and 20 fluorine atoms.

3. A composition of claim 2 wherein the fluoroacyl moiety comprises between 2 and 5 carbon atoms and 1 fluorine atom.

4. A composition according to claim 2 wherein the fluoroacyl group is fluoroacetyl.

5. A composition in accordance with claim 2 wherein the amount of fluoroacyl moiety is between 0.05 and 0.5% by weight.

6. A fluoroalkoxy ester of a partially carbomethoxylated cellulose composition of claim 1 wherein a predetermined number of sites have been carbomethoxylated and a predetermined number of said carbomethoxylated sites are fluoroalkoxylated wherein the weight of said fluoroalkoxy groups is between 0.05 and 5% by weight of the total composition, wherein said fluoroalkoxy moieties comprise the even-carbon ω-fluoro alcohols containing from 2 to 16 carbon atoms.

7. A composition according to claim 6 wherein the alkoxy groups contain from 2 to 6 carbon atoms.

8. A composition according to claim 7 wherein said alkoxy groups comprise 2 carbon atoms and 1 fluorine atom.

9. A composition according to claim 8 wherein the fluoroalkoxy groups comprise between 0.05 and 0.5% by weight of the total composition.

10. A composition of claim 2 wherein the cellulose is in the form of wood, said wood having been partially fluoroacetylated to provide said composition.

11. A composition of claim 1 in dust form, having a particle size of between 5 and 75 microns.

12. A composition in accordance with claim 1 molded in the form of a bait block.

13. A method of combatting termites which comprises providing a termiticidal composition in accordance with claim 1 to a location proximate to termite nests.

14. A method of combatting termites which comprises providing a termiticidal composition in accordance with claim 2 to a location proximate to termite nests.

15. A method of combatting termites which comprises providing a termiticidal composition in accordance with claim 6 to a location proximate to termite nests.

16. A method of combatting termites which comprises injecting a dust composition of claim 11 into the interstitial cavities of a structure subject to termite attack.

17. A method of preparing a composition of claim 2 which comprises reacting cellulose with a fluoroalkanoic acid in the presence of a carbodiimide and a base.

18. A method in accordance with claim 17 wherein there is utilized an excess of carbodiimide relative to the fluoroalkanoic acid.

19. A method of preparing a compound of claim 2 which comprises reacting cellulose with fluoroacylchloride in the presence of a base.

20. A method of preparing a composition of claim 6 which comprises reacting partially carboalkoxylated cellulose with a fluoroalkanol in the presence of a carbodiimide and a base.

21. A process of claim 20 wherein the fluoroalkanol has 1 to 6 carbon atoms substituted by 1 to 6 fluorine atoms provided that the substitution shall not exceed one fluorine atom per carbon atom.

* * * * *